United States Patent [19]
McMillian et al.

[11] 3,946,374
[45] Mar. 23, 1976

[54] RATE-OF-CHANGE COMBUSTION AND CONTAMINATION DETECTION DEVICE

[75] Inventors: Lonnie S. McMillian; George E. Frohwein, both of Huntsville, Ala.

[73] Assignee: SCI Systems, Inc., Huntsville, Ala.

[22] Filed: Dec. 13, 1973

[21] Appl. No.: 424,305

Related U.S. Application Data

[60] Division of Ser. No. 63,646, Aug. 13, 1970, Pat. No. 3,798,625, which is a continuation-in-part of Ser. No. 7,444, Jan. 2, 1970, abandoned.

[52] U.S. Cl. .............................. 340/237 S; 250/381
[51] Int. Cl.² ..................... G08B 17/10; H01J 39/28
[58] Field of Search ............................... 340/237 S; 250/381–385

[56] References Cited
UNITED STATES PATENTS

| | | | |
|---|---|---|---|
| 3,233,100 | 2/1966 | Lampary | 340/237 S X |
| 3,516,083 | 6/1970 | Meyer | 340/237 S |
| 3,548,205 | 12/1970 | Ogden | 307/232 |
| 3,559,196 | 1/1971 | Scheidweiler | 340/237 S |
| 3,778,796 | 12/1973 | Honda | 340/237 S X |

FOREIGN PATENTS OR APPLICATIONS

| | | | |
|---|---|---|---|
| 1,088,836 | 11/1963 | United Kingdom | 340/237 S |

*Primary Examiner*—John W. Caldwell
*Assistant Examiner*—Daniel Myer
*Attorney, Agent, or Firm*—Curtis, Morris & Safford

[57] ABSTRACT

An ionization-type gas contamination detector, intended primarily for use as a fire detector, in which a substance which emits predominantly low-energy beta particles is used as an ionizing radiation source in an ionizing chamber. Rapid changes in ionization current, which indicate the present of a fire or smoke preceding a fire, are detected and an alarm is energized by a rate-of-change circuit in response to such changes. The output of the ionization chamber is amplified, and a level detector energizes the alarm when the amplified chamber output reaches a predetermined level. The output of the amplifier is adjusted relatively slowly to a reference level. In one embodiment, the amplifier output is adjusted to the reference level by the activation of a sample-and-hold feedback loop for a short period of time. In another embodiment, continuous feedback through a circuit with a relatively long time constant provides the desired adjustment. This feature makes the device relatively insensitive to normal atmospheric and environmental changes, while being very sensitive to changes in the level of combustion products in the atmosphere.

11 Claims, 10 Drawing Figures

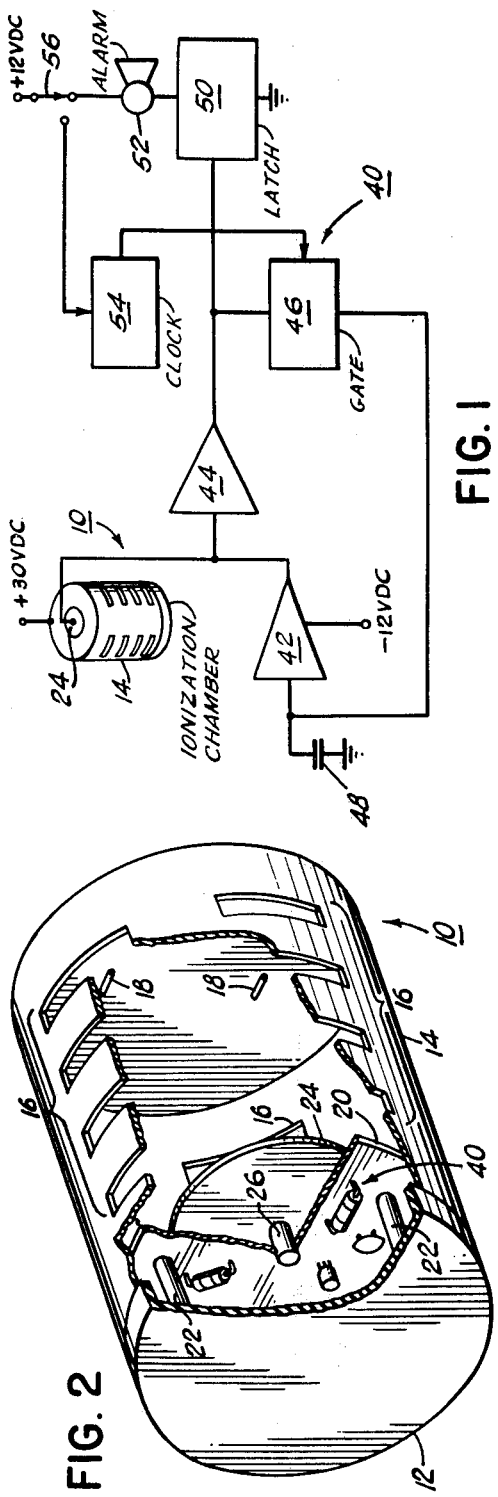
FIG. 1
FIG. 2
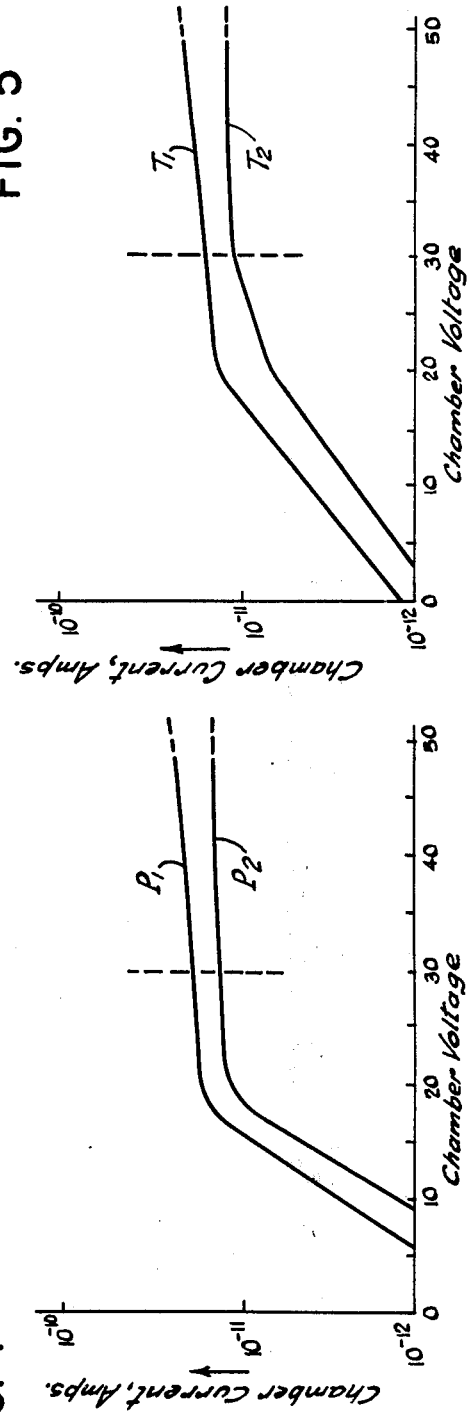
FIG. 5
FIG. 4

RATE-OF-CHANGE COMBUSTION AND CONTAMINATION DETECTION DEVICE

This application is a division of U.S. application Ser. No. 63,646, filed Aug. 13, 1970, now U.S. Pat. No. 3,798,625, which is a continuation-in-part of U.S. application Ser. No. 7,444, filed Jan. 2, 1970, now abandoned.

This invention relates to detection apparatus, and more particularly to fire and gas contamination detection apparatus, and to electronic rate-of-change circuits and ionization chamber devices used in such apparatus. In an illustrative embodiment described herein, the invention takes the form of an ionization-type fire alarm system.

It is an object of the present invention to provide fire and gas contamination detection apparatus which is very sensitive to rapid changes in the condition or composition of the ambient gas, but which is relatively insensitive to long-term changes in such parameters.

Another object of the present invention is to provide ionization-type detection apparatus having an ionization chamber which does not emit any substantial amount of radiation harmful to man.

Yet another object of the present invention is to provide very sensitive rate-of-change electronic detection circuitry suitable for use in the above-described detection apparatus.

These and other objects are met, in accordance with the present invention, by the provision of an ionization-type gas contamination detector, intended primarily for use as a fire detector, in which nickel 63, or other substances which emit predominantly low energy beta particles, e.g. carbon 14, is used as an ionizing radiation source in an ionizing chamber. Rapid changes in ionization current, which indicate the presence of a fire, are detected and an alarm is energized by a rate-of-change circuit in response to such changes. The output of the ionization chamber is amplified, and a level detector energizes the alarm when the amplified chamber output reaches a pre-determined level. The output of the amplifier is returned to a pre-determined reference level by a feed-back loop, thus making the device relatively insensitive to normal atmospheric and environmental changes.

The invention will now be described with the assistance of the drawings in which:

FIG. 1 is a schematic diagram of one embodiment of the electronic detection system of the present invention;

FIG. 2 is a perspective view, shown partly broken away, of ionization chamber apparatus of the present invention;

FIGS. 4 and 5 are graphs showing the variation of certain operating parameters of the ionization chamber shown in FIG. 2;

GENERAL DESCRIPTION

Figure 3:
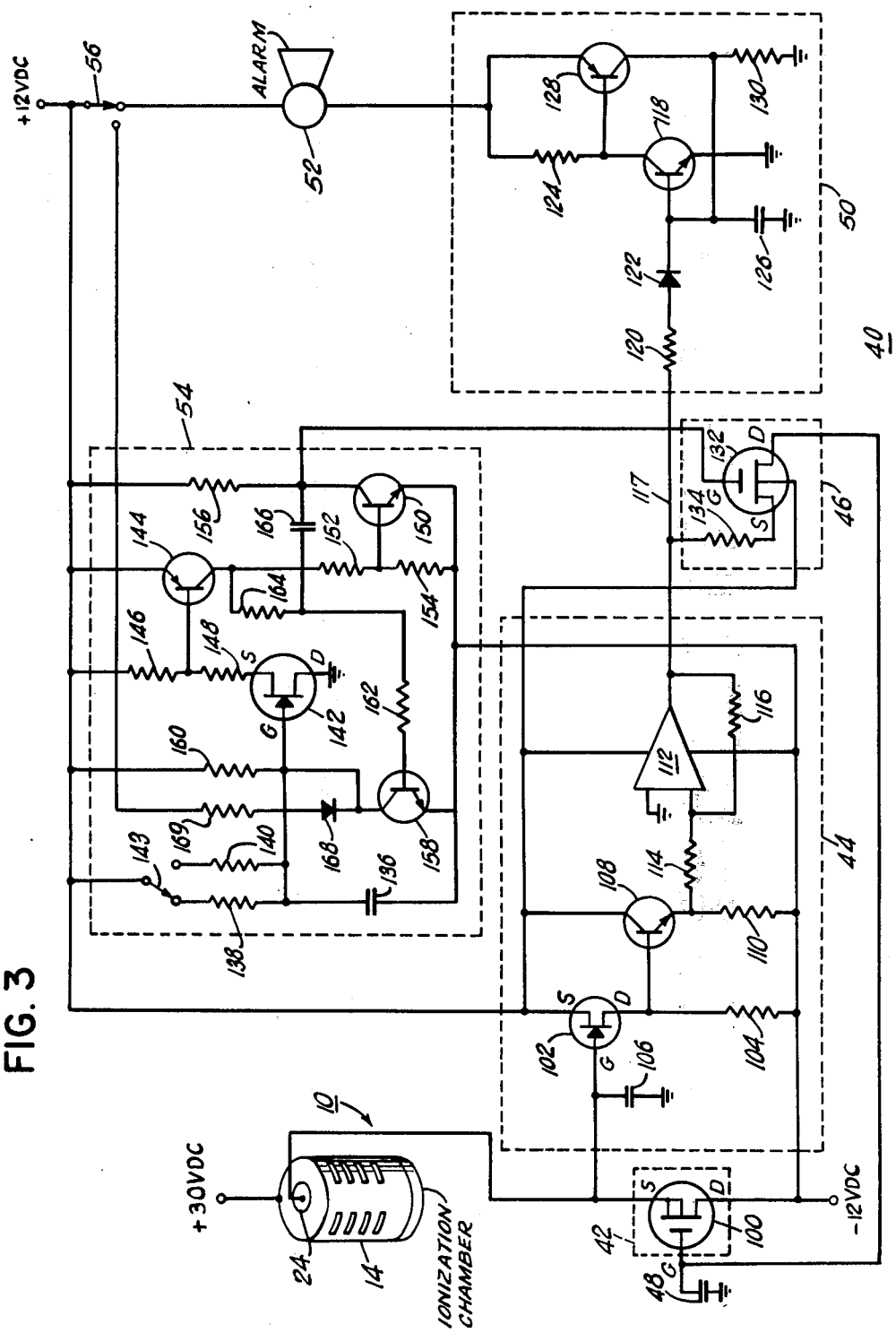
FIG. 3 is a detailed schematic circuit diagram of the system shown in FIG. 1.

The system shown in FIG. 1 of the drawings is intended for use primarily as a fire detector and alarm system. The entire system includes an ionization chamber 10 which contains a radiation source which ionizes the ambient air and produces an ionization current which is inversely proportional to the amount of heavy gas molecules or other contaminants in the air. A detector circuit 40 sets off an alarm 52 when the rate of change in the ionization current is above a certain level, but does not respond to relatively low rates of change caused by normal, slow temperature and pressure changes in the air, and other changes in ambient conditions.

As is well known, fires and developing fires in the pre-combustion stage usually cause rapid increases in the concentration of heavy molecules in the air, and corresponding decreases in ionization chamber currents. The system shown in FIG. 2 detects such changes and activates the alarm 52 to warn that a fire has started or is about to start.

THE IONIZATION CHAMBER

Referring next to FIG. 2, the ionization chamber 10 of the present invention includes a tubular housing 14 (shown partly broken away). The housing 14 is made of metal, except for an insulating plate 12 at one end. The housing has a plurality of slots or openings 16 to permit the gas under test to readily enter the housing.

Two radioactive sources 18 are attached to the metal end wall of housing 14. An electronic circuit board 20 (shown partly broken away) is attached to the insulating base 12 by a plurality of insulating posts 22. A metal collector disc 24 is fastened to the circuit board 20 by means of a conducting member 26, which serves to rigidly support the collector disc 24 and to electrically connect disc 24 to the detector circuit 40 which is formed on the circuit board 20.

The metal housing 14 and the collector disc 24 form the electrodes of the ionization chamber 10. Radioactive sources 18 emit beta particles into the gas under test in the housing 14. The beta particles emitted by the radioactive sources 18 ionize the gas through which they pass. If a voltage is applied between the electrode 14 and the collector disc 24, a small ionization current will flow between the electrodes 14 and 24 due to the presence of ions within tubular member 14.

Radioactive sources 18 emit predominantly low-energy beta particles, which are less harmful to humans than other types of radioactive emission. A preferred material for the sources 18 is carbon 14 ($C^{14}$), nickel 63 ($Ni^{63}$), tritium ($H_3$), or technetium 99 ($Tc^{99}$), each of which emits beta particles almost exclusively and thus makes the ionization chamber of the present invention substantially safer than chambers employing sources rich in alpha particles and gamma rays.

Each of the sources 18 preferably is a segment of cylindrical wire. The wire segments are parallel to one another and are spaced from one another so as to provide a relatively uniform flux of beta particles.

As is shown in FIG. 1, the electrodes 14 and 24 are connected to the detection circuit 40. The presence of gas contaminants within the tubular member 14, such as heavy molecules produced by combustion, or dust, will interfere with the motion of the ionized particles and electrons so as to reduce the current between electrode 14 and collector disc 24.

DETECTOR CIRCUIT

Referring to FIG. 1, the operation of the detector circuit 40 now will be explained. Electrode 14 is connected to a source of positive DC bias voltage, e.g.

+30V DC. Collector disc 24 is connected to a current amplifier 42. Current amplifier 42 is connected to a negative DC bias voltage, e.g. −12V DC. It is believed that beta particles (electrons) interact with air molecules and create positive and negative ions in the chamber 10. The positive ions flow towards the collector disc 24, and the negative ions flow towards the electrode 14. Thus, in the conventional notation, current flows to the collector disc from the electrode 14 and through the current amplifier 32. Changes in this current result in changes in the voltage of electrode 24.

The voltage at electrode 24 is amplified by a voltage amplifier 44. A gate 46 is used to activate a negative feed-back loop for the amplifier 44. When the gate 46 is closed, the output of amplifier 44 is connected to the input of amplifier 42, creating a feed-back loop which operates to drive the output of the amplifier 44 towards zero, by varying the current through the amplifier 42 so as to make the voltage at electrode 24 approach zero.

When the gate 46 is opened, the voltage at electrode 24 is initially maintained at its previous value by a capacitor 48, which stores and maintains the previous feed-back signal for the current amplifier 42. The feed-back loop now is disabled so that any change in the current through the ionization chamber will result in a substantial change in the output voltage of the amplifier 44.

A latching circuit 50 is connected in series with an alarm 52 and is connected to the output of the amplifier 44. A predetermined positive voltage level at the output of the amplifier 44 will cause the latching circuit 50 to conduct and latch, energizing the alarm 52.

The gate 46 is controlled by a clock circuit 54 so as to periodically open and close the feed-back loop. During the time intervals when the gate 46 is closed, the current through the amplifier 42 is readjusted to correct for changes in the chamber conditions, such as temperature and pressure, and for amplifier drift. During the time intervals when the gate is open, referred to as the operating intervals, the circuit operates as a rate-sensitive alarm, since a specific change in ionization current during a single operating interval is required to sound the alarm 52. The specific rate required to sound alarm 52 is electronically determined and may be changed by varying the triggering level of latch 50, the open-loop gain of amplifier 44, or the duration of the operating interval of clock 54.

A reset switch 56 is provided to silence the alarm by simultaneously de-energizing latch 50 and resetting the clock circuit 54 into the condition in which the gate 46 is closed, thereby readjusting the current through amplifier 42 to the new operating conditions.

Referring to FIG. 3, the details of electronic circuit 40 will now be explained.

Current amplifier 42 comprises a p-channel, metal-on-silicon, field effect transistor 100 connected in a source-follower configuration, with ionization chamber 10 serving as the impedance load. A field effect transistor 100 is employed because the current through ionization chamber 10 is extremely small, necessitating the use of a current amplifier capable of delivering extremely small currents. Furthermore, field effect transistor 100 has a high input impedance to prevent the discharging of capacitor 48 during the operating intervals when gate 46 is open.

Amplifier 44 is a three-stage semiconductor amplifier. The first stage, connected to electrode 24, consists of a field effect transistor 102 in source-follower configuration, with a resistor 104 serving as the impedance load. A field effect transistor 102 is employed to provide an extremely high input impedance to prevent loading of the ionization chamber. A capacitor 106 is also connected to electrode 24, to reduce the high frequency response of amplifier 44 and to bypass to ground any 60 cycle AC signals which might be induced in the ionization chamber circuit.

The output of the source-follower stage is connected to the base of a second stage transistor 108, which is connected in an emitter-follower configuration with a resistor 110 serving as the emitter load resistor.

The output of emitter-follower stage is coupled to an integrated circuit operational amplifier 112 through a resistor 114. A resistor 116 couples the output of operational amplifier 112 with its input, to provide negative feedback and thus limit the gain of operational amplifier 112. Source-follower transistor 102 and emitter follower transistor 108 provide current gain for the voltage signal present at electrode 24. Operational amplifier 112 provides voltage gain for this signal, so that the voltage gain of amplifier 44 is essentially determined by resistors 114 and 116, which determine the gain of operational amplifier 112.

The output lead 117 of the operational amplifier 112 is connected to the latching circuit 50. The latching circuit 50 includes a transistor 118, and the lead 117 is connected to the base lead of transistor 118 through a resistor 120 and a diode 122. Transistor 118 is connected in a common-emitter configuration, with a resistor 124 and alarm 52 providing the collector load. Transistor 118 normally is non-conducting. The appearance of a positive voltage above a predetermined level on the output lead 117 of the operational amplifier 112 will provide base drive current for transistor 118, and will cause it to conduct. The level of voltage required is determined by the value of resistor 120. Diode 122 prevents transistor 118 from being damaged by excessive negative bias should the output of operational amplifier 112 be negative. A capacitor 126 is connected to the base of transistor 118 to reduce the high frequency response of latching circuit 50 to avoid false alarms which otherwise might be caused by transient voltages at the output of operational amplifier 112.

The collector lead of transistor 118 is connected to the base of another transistor 128, which is connected in common emitter configuration, with a resistor 130 serving as a collector load resistor. Transistor 128 also normally is non-conducting. When transistor 118 conducts, the voltage at the base of transistor 128 will be substantially reduced, causing transistor 128 to conduct. Alarm 52, which is in series with transistors 118 and 128, will thus be energized when transistors 118 and 128 are caused to conduct by the presence of the predetermined positive voltage level at the output of operational amplifier 112.

The latching function of latching circuit 50 is provided by the connection of the collector of transistor 128 to the base of transistor 118 so as to provide positive feed-back to transistor 118. This positive feedback signal will cause transistor 118, and thus transistor 128, to remain conducting despite any change in the output voltge of operational amplifier 112. Thus, due to the positive feed-back signal, alarm 52 will continue to be energized despite any change in the output voltage of operational amplifier 112.

Gate circuit 46 comprises a p-channel, metal-on-silicon field effect transistor 132, employed as a switch. The output signal from operational amplifier 112 is conducted to transistor 132 through a resistor 134 which is connected to the source of transistor 132. The drain of transistor 132 is connected to the input of current amplifier 42. The substrate of transistor 132 is connected to the +12 volt DC supply, so that a negative voltage applied to the gate of transistor 132 will cause it to conduct, thereby conducting the output signal of operational amplifier 112 to the input of current amplifier 42 and to the capacitor 48.

The signal for the gate of transistor 132 is generated by the clock circuit 54, whose operation will be described in sequence, commencing with the start of the operating interval. A capacitor 136 is connected in series with one of two resistors 138 and 140, depending upon the position of a sensitivity selection switch 142. At the start of the operating interval, capacitor 136 will be substantially discharged. Thereafter, it will charge at a rate determined by the RC time constant of resistor 138 or 140 and capacitor 136, depending upon which position switch 143 is in. Capacitor 136 charges until it reaches a voltage level sufficient to cause a junction field effect transistor 142 to conduct. The gate of transistor 142 is connected to the junction of capacitor 136 and resistors 138 and 140. The charging time of capacitor 136 determines the operating time interval of the detection circuit 40, and the length of that time interval is a factor in the determination of the sensitivity of the system. A longer time interval, corresponding to the use of the larger of the resistors 138 and 140, produces greater sensitivity, since the required change in ionization current may occur over a longer time interval. The rate of change detection sensitivity of the circuit 40 is, therefore, varied by operation of switch 143. The preferred operating time intervals employed in typical fire alarm system using the invention vary from 15 seconds to several minutes.

The base of a transistor 144 is connected to the load resistors 146 and 148 of transistor 142. Transistor 144 is normally conducting, so that it will assume a non-conducting state when transistor 142 conducts. The base of transistor 150 is connected to the collector load resistors 152 and 154 of transistor 144. Transistor 150 is normally non-conducting, so that it will conduct when transistor 144 assumes a non-conducting state. A resistor 156 serves as a collector load resistor for transistor 150. The collector of transistor 150 is connected to the gate of transistor 132 in the gating circuit 46, so that transistor 132 will conduct when transistor 150 conducts.

The base of a transistor 158, connected in a common-emitter configuration, with a resistor 160 serving as a collector load, is connected to transistor 144 and 150 through a RC network comprising a pair of resistors 162 and 164 and a capacitor 166. Transistor 158 is normally non-conducting. After a time interval, during which capacitor 166 is charging, transistor 158 will conduct. This causes capacitor 136 to discharge through transistor 158, and thus resets transistors 142, 144, and 150 to their initial condition. Transistor 150 is once again non-conductive, thereby causing transistor 132 to assume a non-conducting state. This second time interval during which transistor 132 is conductive, corresponds to the time interval during which the negative feedback loop for amplifier 44 is closed. In a typical fire alarm system, this time interval is substantially shorter than the operating time interval, and usually is several seconds long.

Reset switch 56 serves a dual function. When actuated, reset switch 56 disconnects the +12V supply from the alarm 52 and latching circuit 50, thereby silencing the alarm and disabling the latching circuit. In addition, gate drive current to transistor 142 is supplied through a resistor 169, causing transistor 142 to conduct, therby placing the clock circuit in the condition in which transistor 132 is conductive. This closes the negative feedback loop for amplifier 44, so that the output of operational amplifier 112 will once again be driven to zero. This insures that the input to the latching circuit 50 will be zero and that the alarm will remain in an off condition immediately after release of the reset switch 56.

IONIZATION CHAMBER OPERATING PARAMETERS

FIGS. 4 and 5 show the voltage-current characteristics of an ionization chamber 10 which has been built and successfully tested. This chamber had the following dimensions:

Housing 14 diameter - 3 inches
Collector disc 24 diameter - 2 inches
Spacing from collector disc 24 to radioactive sources 18 - 4 cm.
Radioactive sources 18 - 100 microcuries $Ni^{63}$ FIG. 4 is a graph showing the voltage-current characteristics of the chamber 10 at two different ambient gas pressures, $P_1$ and $P_2$. Pressure $P_1$ is approximately equal to atmospheric pressure at sea level, and $P_2$ is approximately equal to atmospheric pressure at an altitude of 10,000 feet. Applicants have recognized that operation of the chamber 10 at bias voltages below the "knees" in the curves $P_1$ and $P_2$, i.e., at voltages less than about 20 volts, will make the ionization current unduly sensitive to ambient gas pressure changes. Applicants also have recognized that the spacing between the curves $P_1$ and $P_2$ increases as the voltage is increased much above about 40 volts, with the result that the sensitivity to pressure changes will increase with increasing chamber voltages above that level. Thus, the ideal bias voltage range is within the saturation region of the chamber, identified by the nearly horizontal portions of the curves $P_1$ and $P_2$, but not far into the saturation region. In the specific example depicted in FIGS. 4 and 5, the preferred range is 20 to 40 volts, and the preferred voltage is 30 volts. The preferred region of operation is referred to herein as the "low-voltage saturation region".

FIG. 5 is a graph similar to that of FIG. 4, except that the gas pressure remains constant while the gas temperature is changed from $T_1$ and $T_2$. $T_2$ is approximately 10° centigrade and $T_1$ is approximately 60° centigrade. Once again, the best operating region proves to be the low-voltage saturation region, since voltages above or below this region produce greater sensitivity to gas temperature changes. A voltage of 30 volts is best for the specific configuration whose operation is depicted in FIG. 5.

CONTINUOUS FEEDBACK EMBODIMENTS

Figure 6:
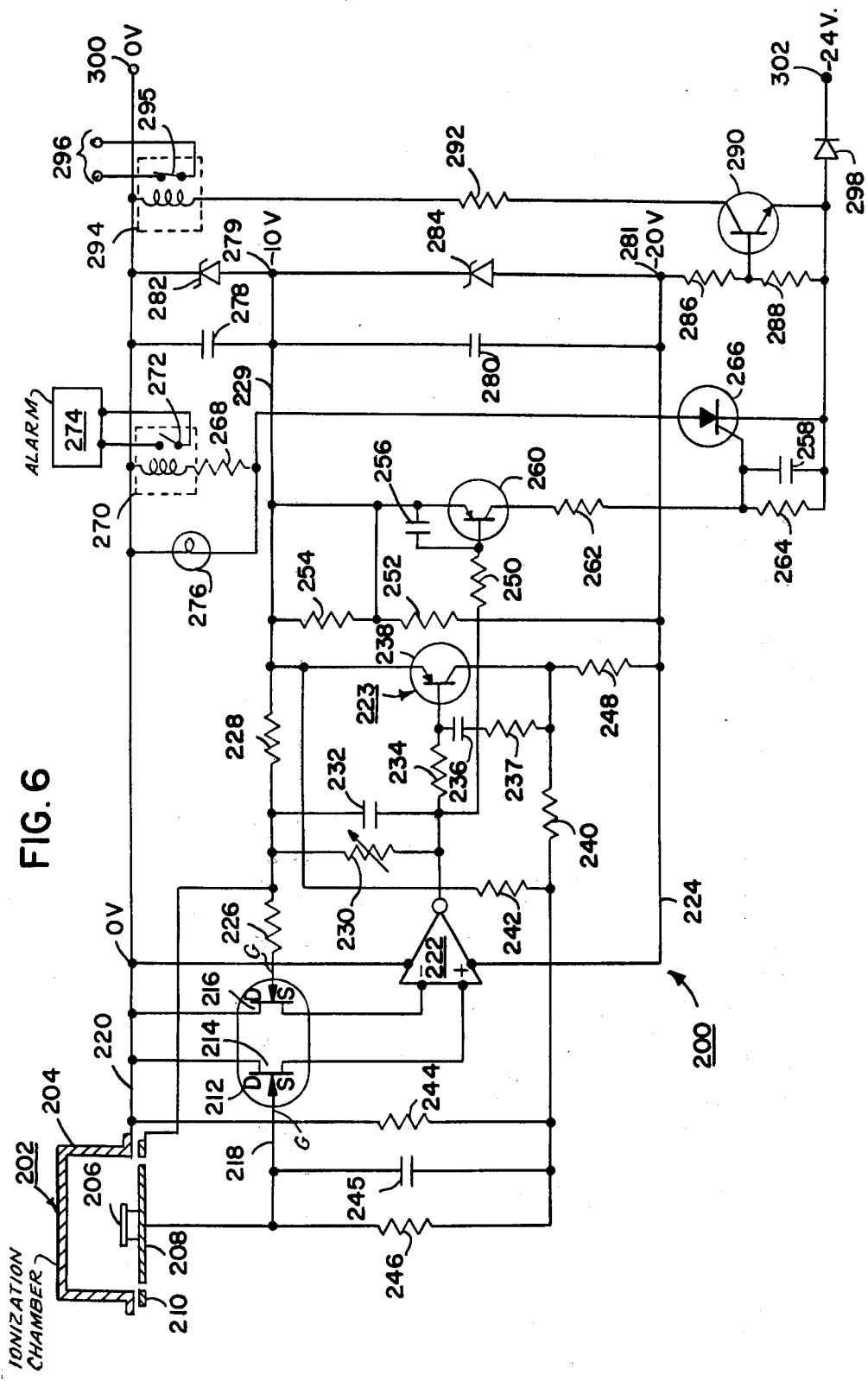
FIGS. 6, 7, 8 and 10 are schematic drawings of further embodiments of the invention.

The combustion detector 200 shown in FIG. 6 includes an ionization chamber 202 having a beta particle collector housing 204, a radiation source 206 which is attached to an anode plate 208. In addition, a "guard ring" 210 is provided. The guard ring 210 surrounds the anode plate 208 and is maintained at substantially the same voltage as the anode plate in order to intercept and collect stray currents which otherwise might flow to the anode plate. Ambient air can enter and leave the chamber through the gap between the plate 208 and the housing 204.

The radiation source 206, like the source 18, produces predominantly beta particles and preferably consists of carbon 14 ($C^{14}$).

The collector housing 204 of chamber 202 is connected to a line 220 which is at zero potential. The anode plate 208 of the chamber is supplied with a negative bias voltage which appears on a lead 218. Thus, a voltage is applied across the ionization chamber.

The lead 218 is connected to the gate electrode of a first field effect transistor (FET) 214 of a pair 212 of matched junction FET's 214 and 216. As in the previous embodiments, the use of a field effect transistor as the first stage in the amplification chain presents a very high input impendence to the anode 208. The signal from each of the FET's is conducted to one of two input leads of a high-gain operational differential amplifier 222. By using matched FET's, the FET gate-source voltage drop components of the voltages at the two inputs to the amplifier 222 will be approximately equal and will be balanced-out by the differential operation of the amplifier.

The output signal from the amplifier 222 is conducted to an integrating circuit 223 consisting of a resistor 237, a capacitor 236, a resistor 234 and a transistor 238. The output of this integrating circuit appears across the load resistor 248 and is fed back to the input of the field effect transistor pair 212 through a resistive network including resistors 240, 242, 244 and 246. The amplifier 222 amplifies the signal it receives from the ionization chamber 202. This signal is integrated by the integrating circuit and the signal from the integrator is fed back to change the bias signal on FET pair 212, thus changing the input bias for the amplifier 222 and reducing its output signal. The output of the amplifier 222 is conducted to an alarm circuit (to be described) which produces an alarm signal when the level of the output of amplifier 222 reaches a predetermined value.

The values of the resistors 234 and 237, the capacitor 236, and the other components in the feedback network are chosen so as to give the network a relatively long time constant. For example, a time constant of 20 minutes has been found to be desirable and practical. Thus, the integrator circuit provides a negative feedback signal which increases relatively slowly with time. The reason for this is to make the device sensitive to combustion products which accumulate relatively rapidly, thus indicating a fire or incipient fire, and yet prevent the device from alarming in response to relatively slowly-changing atmospheric conditions. For example, with a time constant of twenty minutes or thereabouts, the device has alarmed in response to an accumulation of smoke emitted by smoldering wood, but does not alarm when atmospheric pressure or temperature, etc., change at an ordinary rate. After a relatively long time, the negative feedback circuit will return the bias signal on the FET pair 212 to approximately its original value. Thus, relatively slow changes in ionization current will be cancelled out by the system.

Referring now to the right-hand portion of FIG. 6, an alarm device 274 is energized by means of a transistor 260 which energizes a silicon-controlled rectifier (SCR) 266 which, in turn, energized a relay 270 to close a switch 272 and turn on the alarm device. The base lead of the transistor 260 is connected through a resistor 250 to the output of amplifier 222. A capacitor 256 is connected between the base lead and the emitter lead of transistor 260. The RC circuit formed by the resistor 250 and the capacitor 256 delays the build-up of input signal to the transistor 260 for a relatively short length of time in order to insure that the signal being received is not caused by transients such as those which might occur due to puffs of air being blown into the ionization chamber 202.

When the output of the amplifier 222 reaches a predetermined level, which is determined by a pair of resistors 252 and 254 connected in a voltage divider arrangement, and after the slight time delay mentioned above, transistor 260 turns on and conducts current through a load resistor 262. The load current flows through another resistor 264 with a capacitor 258 connected in parallel with it and to the gate lead of the SCR 266 to turn the SCR on. This causes current to flow through the SCR, through a voltage dropping resistor 268 and the coil of relay 270 to close the contact 272 and energize the alarm 274. Also, a lamp 276 is lighted to indicate that the device 200 is in an alarm condition. The alarm device 274 itself may be situated at a remote location, particularly if the fire detection unit 200 is merely one of an extensive fire detection system. The SCR 266 will remain latched in the "on" condition until the voltage applied to it is removed for approximately 15 seconds. This can be done by a switch (not shown) whose operation will reset the alarm device 274.

The integrator device 223 is commonly known as a "Miller" integrator. The transistor 238 is used for amplification and inverting functions, as well as its functions in the integrator circuit. The resistor 237 stabilizes the ciruit and reduces the effect of transients.

The resistors 240 and 242 comprise a voltage divider network which reduces the gain in the feed-back loop and reduces the rate at which the feed-back voltage increases. The resistance of resistor 240 is ten times that of resistor 242; resistor 240 has a preferred resistance of two megohms, and resistor 242 has a resistance of 200,000 ohms.

Resistor 244 is a relatively large (e.g. 4.7 megohms) resistor which is used to adjust the bias level of the chamber housing 204. Resistor 246 is a very large resistor (e.g., 1,000 megohms) which converts ionization current changes into voltages, without unduly loading the chamber. Capacitor 245 is connected across resistor 246 in order to filter out stray 60 Hz and high-frequency noise signals which might be picked up in the circuit. Another 60 Hz and noise filter capacitor 232 is connected between the output of the amplifier 222 and a line leading to the gate lead of FET 216. A variable resistor 230 is connected between the same two points in order to adjust the gain of the amplification provided by the FET pair 212 and the amplifier 222.

The guard ring 210 is connected to the gate lead of FET 216 through a very large (e.g. one thousand megohms) resistor 226. Thus, because of the high input gate impendances of the FETs, the guard ring 210 is maintained at substantially the same potential as the anode plate 208.

POWER SUPPLY

A 24 volt direct current supply signal is applied to input terminals 300 and 302. A steady, regulated voltage of negative 10 volts is maintained on line 229 by the connection of a Zener diode 282 and a filter capacitor 278 between the input lead 300 and the point 279. Similarly, regulated voltage of negative 20 volts is maintained between points 279 and 281 by means of a second Zener diode 284 and filter capacitor 280.

Two "trouble" contacts 296 are provided. The appearance of a closed circuit at those terminals indicates that line voltage is being supplied to the fire alarm system, and that Zener diodes 280 and 284 have not been short circuited. The relay is maintained in an energized condition by current flowing to its coil through a transistor 290, and this keeps the contact 295 of the relay closed. Transistor 290 receives bias energization by means of a voltage divider consisting of two resistors 286 and 288 whose midpoint is connected to the base lead of transistor 290, and the combination is connected between the negative 24 volt line and point 281. When the line opens or one of the Zener diodes 282 or 284 becomes short-circuited, the relay 294 will be de-energized and trouble will be indicated by the open circuit between trouble terminals 296. A diode 298 is connected between the emitter of transistor 290 and the input lead 302.

Following is a table illustrating the specific circuit components which were used in a device which was successfully built and tested in accordance with the embodiment of the invention shown in FIG. 6:

| Part No. | Value or identification |
| --- | --- |
| FET pair 212 | 2 N 3958 |
| Amplifier 222 | Operational differential amplifier SN 72741 sold by Texas Instruments, Corp. |
| Transistors 238 and 260 | 2 N 2907 |
| Transistor 290 | 2 N 697 |
| Resistor 234 | 4.7 megohms |
| Resistor 237 | 470,000 ohms. |
| Capacitor 236 | 640 microfarads |
| Resistor 248 | 110,000 ohms. |
| Resistor 240 | 2 megohms |
| Resistor 242 | 200,000 ohms. |
| Resistor 244 | 4.7 megohms |
| Resistor 246 | 1000 megohms |
| Capacitor 245 | 500 Picofarads |
| Resistor 226 | 1000 megohms |
| Resistor 228 | 100 ohms. |
| Capacitor 232 | 2 Microfarads |
| Resistor 254 | 4,700 ohms. |
| Resistor 254 | 4,700 ohms. |
| Resistor 250 | 10,000 ohms |
| Capacitor 256 | 4.7 microfarads |
| Resistor 262 | 2000 ohms. |
| Resistor 254 | 1000 ohms. |
| Capacitor 258 | 4.7 Microfarads |
| SCR 266 | 2 N 5960 |
| Capacitors 278 and 280 | 125 Microfarads |
| Zener diodes 282 and 284 | 1 N 758 |
| Resistor 286 | 160 ohms. |
| Resistor 288 | 500 ohms. |
| Resistor 268 | 570 ohms. |
| Resistor 292 | 860 ohms. |
| Diode 298 | 1 N 4006 |

Each of the 1,000 megohm resistors preferably consists of a rod of ceramic material with a metal oxide and ceramic coating. Such resistors are sold by Welwyn, Inc. The capacitor 236 preferably is a low-leakage capacitor with polycarbonate film dielectric material, sold by Cornell-Dublier.

Figure 7:
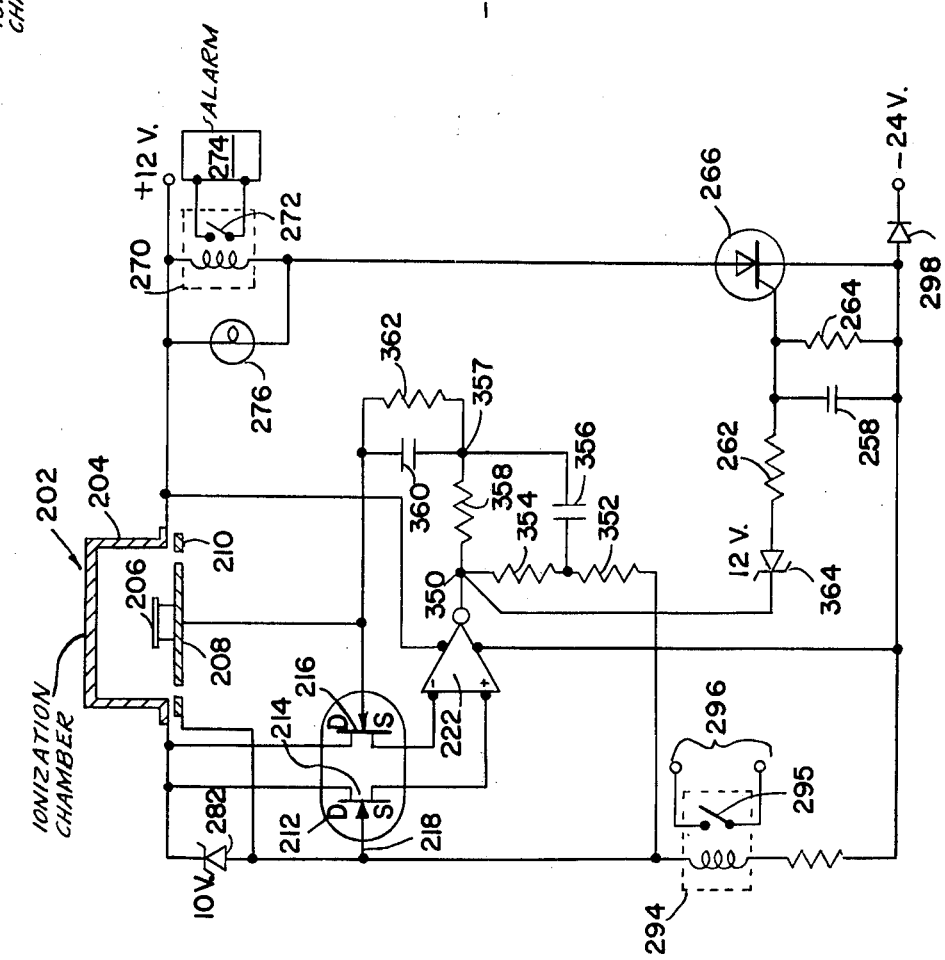

The preferred embodiment of the present invention is shown in FIG. 7 of the drawings. The circuit shown in FIG. 7 is, in substance, the same as that shown in FIG. 6, except that the circuit is considerably simplified so as to reduce the number of components. The same reference numerals are used for the same components in both FIGS. 6 and 7. The most important changes are in the feed-back network from the amplifier 222, and only those changes will be described in detail.

A 100,000 ohm resistor 354 is connected to the output lead of the amplifier 222 at a terminal 350. A 5 microfarad polycarbonate, low-leakage capacitor 356 is connected to the opposite terminal of resistor 354, as is a 100 ohm resistor 352. The other terminal of resistor 352 is connected through the low-impedance path of the coil of relay 294 to the negative terminal of the power supply. A 5,000 megohm ceramic resistor 358 is connected between the terminal 350 and the other end of the capacitor 356. The common terminal 357 between resistor 358 and capacitor 356 is connected to a parallel connection of a 500 picofarad capacitor 360 and another 5,000 megohm ceramic resistor 362. That parallel combination is connected to the plate 208 of the ionization chamber 202 and the gate lead of FET 216, to complete the feed-back path. A zener diode 364 is connected between the point 350 and the input of the SCR 266 to set a bias level for the alarm voltage.

Figure 8:
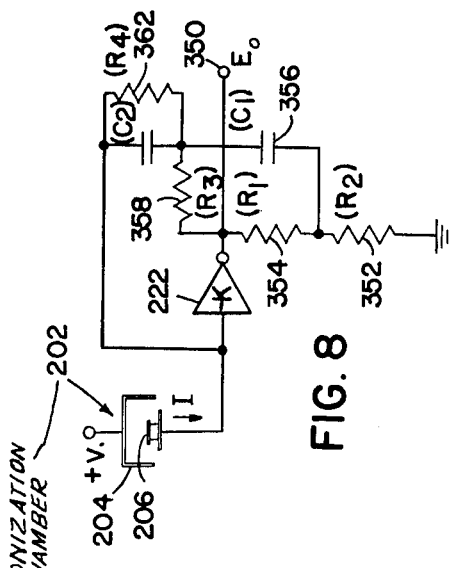

FIG. 8 is a simplified schematic circuit diagram for the feedback amplifier and ionization chamber connections of the circuit shown in FIG. 7. It is believed that the following equation expresses the relationship between a change in input voltage $E_1$ and a change in output voltage $E_0$ at the output terminal 350:

$$\frac{\Delta E_0}{\Delta E_1} = \frac{(R_1 + R_2)}{R_2}$$

In which:

$\Delta E_0$ = the change in output voltage at terminal 350;
$\Delta E_1$ = the change in input voltage;
$R_1$ and $R_2$ are the resistors shown in FIG. 8.

In the above equation, an approximation has been made in view of the following relationships:

a. $R_4 >> R_z$;
b. $(-K)$, the open loop gain of amplifier 222, is $>>(R_1 + R_2)/R_z$;
c. $E_1$ = the change in chamber current, $I_1$, divided by $R_4$.
d. The change in input current to the amplifier 222 $<< I_1$.

Figure 9:
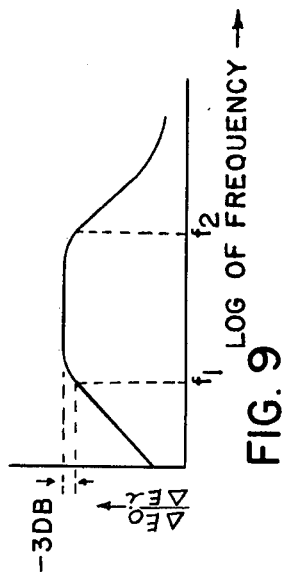
FIG. 9 is graph illustrating certain operational parameters of the invention.

The above equation is believed to hold true for ionization current changes which occur over a time period that is short relative to the time constant of resistor 358 and capacitor 356 and long relative to the time constant of resistor 362 and capacitor 360. FIG. 9 shows the relationship which is believed to exist between the voltage gain of the circuit and the frequency of the input signals. In FIG. 9, the following equations hold true:

$$f_1 = \frac{1}{2\pi R_3 C_1}$$

$$f_2 = \frac{1}{2\pi R_4 C_2}$$

in which $C_1$ and $C_2$ are the capacitors shown in FIG. 8, and $f_1$ and $f_2$ are the frequencies at which the gain has dropped 3 decibels from the maximum. These frequencies indicate the pass band of the circuit.

As is shown in FIG. 9, the circuit gives little or no amplification for relatively high or very low frequency input signals. This prevents the detector from alarming in response either to electrical noise or stray 60 Hz signals (both having relatively high frequency components) or to slowly changing input signals caused by normal atmospheric changes.

The gain of the circuit preferably as 1.0 to D.C. input signals. However, without amplification, signals from the ionization chamber are not large enough to enable the alarm. Slowly changing input signals, such as those caused by changing atmospheric conditions, cause slow increases in output voltage from the amplifier 222. However, those changes are so slow that the alarm level of the amplifier is not reached because the negative feed-back voltage of the feed-back network increases fast enough to prevent the amplifier output from reaching the alarm level.

Input signals having relatively high-frequency components, such as noise spikes and 60Hz signals, flow through the capacitors 360 and 356 and the 100 ohm resistor 352 to ground rather than to the high impedance ($10^{10}$ohms) gate lead of the FET 216. Thus, such high-frequency components are filtered out of the amplifier input.

The frequencies $f_1$ and $f_2$ are selected such that input signals having the frequency components caused by the usual fire will receive full amplification, and signals not having those components will receive reduced amplification. Since the frequency of the components of a signal is a function of the rate of change of the signal, the alarm device is responsive to the rate of change of the combustion products signal.

The alarm device has a "dead-band" in that regardless of the rate of change of the input signal, unless the magnitude of the input signal from the amplifier reaches a certain minimum value, the device alarm remains disabled. This minimizes false-alarming due to small combustion or contamination sources, such as cigarette smoke, etc.

The detector system described above has a number of advantages. It is a very sensitive detector of fires and gas contaminants, and yet it is relatively insensitive to normal ambient temperature and pressure changes. Moreover, these desirable features are obtained with only one ionization chamber, and with the use of reliable solid-state circuitry.

The detector also is relatively small, and thus easily can be made inconspicuous in factories, offices and other structures in which it might be used. The detector also is relatively light in weight, a feature which makes its use highly advantageous in many uses.

The detector utilizes a radiation source, such as carbon 14 or nickel 63, which emits predominantly beta particles, and therefore emits practically no harmful radiation. This makes the device inherently safe for use in human dwellings and permits a reduction in safety maintenance costs. Furthermore, such materials are relatively inexpensive to use as radiation sources.

Figure 10:
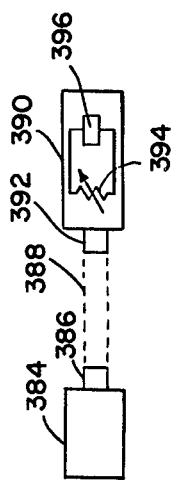

FIG. 10 shows another embodiment of the invention. This embodiment is a so-called "smoke detector", i.e., a detector in which a light source 384 emits light through a lens system 386 in a beam 388. The beam 388 of light is received by an alarm unit 390 which has a lens system 392 and a photoconductor 394 which receives light from the lens system 392.

When smoke or other light-blocking contamination intercepts the light beam 388, the resistance of the photoconductor 394 increases. A known alarm circuit is connected to the photoconductor 394 and alarms in response to the change of resistance, thus indicating the presence of smoke. The smoke detector described so far is conventional.

The lenses of such a system often become coated with dust or other pollutants. This adversely affects the operation of the smoke detector. In accordance with the present invention, the alarm circuit 396 of the present invention is used in place of the conventional alarm circuit. The circuit is connected as shown in FIG. 7, for example, except that the photoconductor 394 replaces the ionization chamber. The resulting detector has the advantage that the usual coating of the lenses is eliminated as a source of alarm signals since the signal changes created by such coating increase very slowly. The effects of such changes are eliminated in the same way that changes due to atmospheric changes are eliminated. Thus, the detector is more reliable and requires less maintenance.

The above description of the invention is intended to be illustrative and not limited. Various changes or modifications in the embodiments described may occur to those skilled in the art and these can be made without departing from the spirit or scope of the invention.

We claim:

1. Gas contamination detector apparatus comprising an ionization chamber readily accessible to the gas under test, means for ionizing the gas in said chamber, means for conducting an electrical current through said chamber, amplification means for producing an output signal which is a function of said current, level detector means for detecting a pre-determined signal level at the output of said amplification means, and bandpass filter means for attenuating the gain of said amplification means with respect to very slow and very rapid changes in said current.

2. Apparatus according to claim 1, in which said amplification means includes at least one field effect transistor and a high-gain voltage amplifier.

3. Apparatus according to claim 2, in which the gate lead of said transistor is connected to said ionization chamber, and said voltage amplifier is an operational amplifier.

4. A combustion indicator, said indicator comprising sensing means for developing an electrical sensing signal which varies with the concentration of combustion products in the ambient air, amplification means for amplifying said sensing signal, means for developing an alarm signal in response to the receipt from said amplification means of a signal of a predetermined alarm level, and time delay negative feedback means for supplying a time-delayed feedback signal to said amplification means to drive the output of said amplification means to a reference level less than said alarm level.

5. Apparatus as in claim 4 in which said feedback means includes an integrator connected between the output and the input of said amplification means.

6. Gas contamination detection apparatus comprising an ionization chamber readily accessible to the gas under test, radioactive means for ionizing the gas in said chamber, means for applying a voltage across said chamber, said voltage being within the low-voltage saturation region of said ionization chamber's voltage-current characteristics, and means for detecting changes in the current through said ionization chamber.

7. Gas contamination detection apparatus comprising an ionization chamber readily accessible to the gas under test, means for ionizing the gas in said chamber, means for conducting an electrical current through said chamber, electrical signal storage means, means for varying said current in response to the signal stored in said storage means, amplification means for producing an output signal which is a function of said current, level detector means for detecting a predetermined signal level at the output of said amplification means, and control means for periodically applying said output signal to said storage means.

8. Apparatus according to claim 7, wherein said current varying means comprises a field effect transistor connected in a drain follower configuration, and said storage means comprises a capacitor connected to the gate of said field effect transistor.

9. Apparatus according to claim 7, in which said amplification means includes at least one metal-oxide-silicon field effect transistor and a high-gain voltage amplifier.

10. Apparatus according to claim 9, in which the gate lead of said transistor is connected to said ionization chamber, and said voltage amplifier is an operational amplifier.

11. A gas contamination detection method comprising the steps of providing an ionization chamber readily accessible to the gas under test, providing radioactive means for ionizing the gas in said chamber, applying a voltage across said chamber, said voltage being within the low-voltage saturation region of said ionization chamber's voltage-current characteristics, and detecting changes in the current through said ionization chamber.

* * * * *